United States Patent [19]

Weng

[11] Patent Number: 5,569,270
[45] Date of Patent: Oct. 29, 1996

[54] LAPAROSCOPIC SURGICAL INSTRUMENT

[76] Inventor: Edward E. Weng, 51077 Sand Shores, Shelby Township, Macomb County, Mich. 48316

[21] Appl. No.: 354,650

[22] Filed: Dec. 13, 1994

[51] Int. Cl.$^6$ .................................................. A61B 17/00
[52] U.S. Cl. .................... 606/144; 606/147; 606/148; 112/169; 600/201
[58] Field of Search ................ 606/1, 151, 205–208, 606/144–148, 139; 227/175.1–175.4, 176.1–182.1, 901, 19; 600/146, 148, 149, 201; 112/80.03, 169

[56] References Cited

U.S. PATENT DOCUMENTS

| | | | |
|---|---|---|---|
| 4,224,947 | 9/1980 | Fukuda . | |
| 4,890,615 | 1/1990 | Caspari et al. | 606/146 |
| 4,923,461 | 5/1990 | Caspari et al. | 606/146 |
| 4,935,027 | 6/1990 | Yoon | 606/146 |
| 5,174,276 | 12/1992 | Crockard | 600/148 |
| 5,195,507 | 3/1993 | Bilweis . | |
| 5,234,460 | 8/1993 | Stouder, Jr. | 606/205 |
| 5,263,956 | 11/1993 | Nobles | 606/130 |
| 5,269,753 | 12/1993 | Wilk | 604/49 |
| 5,275,608 | 1/1994 | Forman et al. | 606/205 |
| 5,281,235 | 1/1994 | Haber et al. | 606/139 |
| 5,282,806 | 2/1994 | Haber et al. | 606/139 |
| 5,308,327 | 5/1994 | Heaven et al. | 604/96 |
| 5,336,231 | 8/1994 | Adair | 606/148 |
| 5,358,508 | 10/1994 | Cobb | 606/174 |
| 5,359,995 | 11/1994 | Sewell, Jr. | 128/20 |
| 5,405,344 | 4/1995 | Williamson et al. | 606/1 |
| 5,454,827 | 10/1995 | Aust et al. | 606/205 |

Primary Examiner—Michael Powell Buiz
Assistant Examiner—Jeffrey A. Schmidt
Attorney, Agent, or Firm—Howard & Howard

[57] ABSTRACT

A surgical instrument provides a simplified method of inserting sutures in laparoscopic surgery. A suture needle is hollow, and the suture thread extends through the needle. A liquid, such as a saline irrigation fluid, is driven through the hollow needle. This liquid carries the suture thread. The suture needle initially passes through the tissue, and the liquid is then actuated to drive the suture thread through the needle. The needle may then be withdrawn, leaving the suture thread in the tissue. The suture thread can then be tied off to complete the suture. In another aspect of this invention, the suture needle, or any other surgical tool, is connected to the body of the surgical instrument through a universal connection such that the angular orientation of the surgical tool relative to the surgical instrument can be universally adjusted in a three dimensional space. In one embodiment, the surgical tool is connected to a ball-shaped structure that is adjustable relative to the body of the surgical instrument. Several rods reciprocate within the body of the surgical instrument between locked and unlocked positions. The surgical instrument is preferably inserted into the patient in a first angular orientation, and the locking structure is then moved to the unlocked position. The angular orientation of the surgical tool can then be adjusted relative to the axis of the surgical instrument. Once the tool is at the desired angular orientation, the locking structure is moved to the locked position, where it holds the surgical tool at the newly adjusted angle.

11 Claims, 2 Drawing Sheets

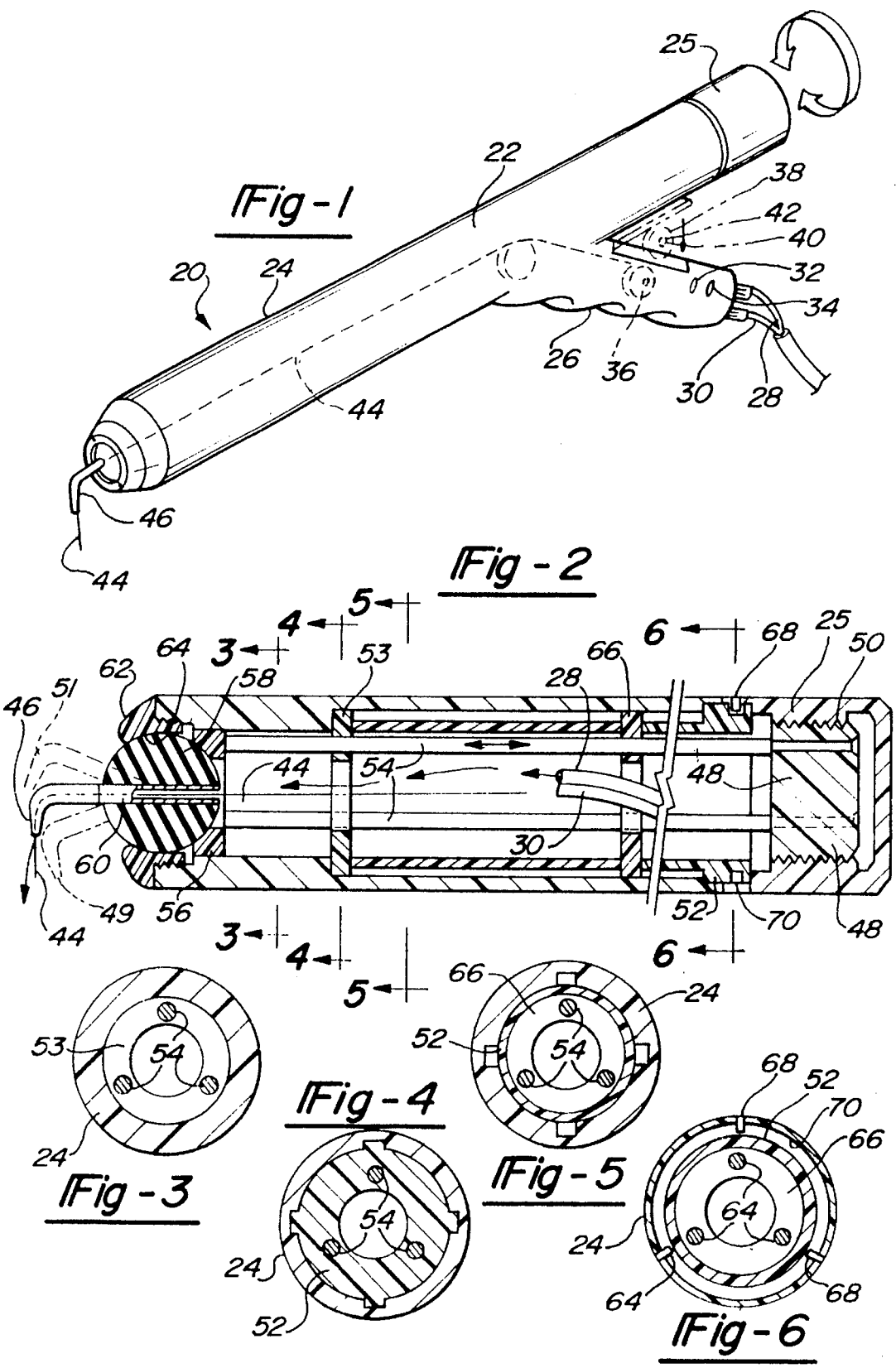

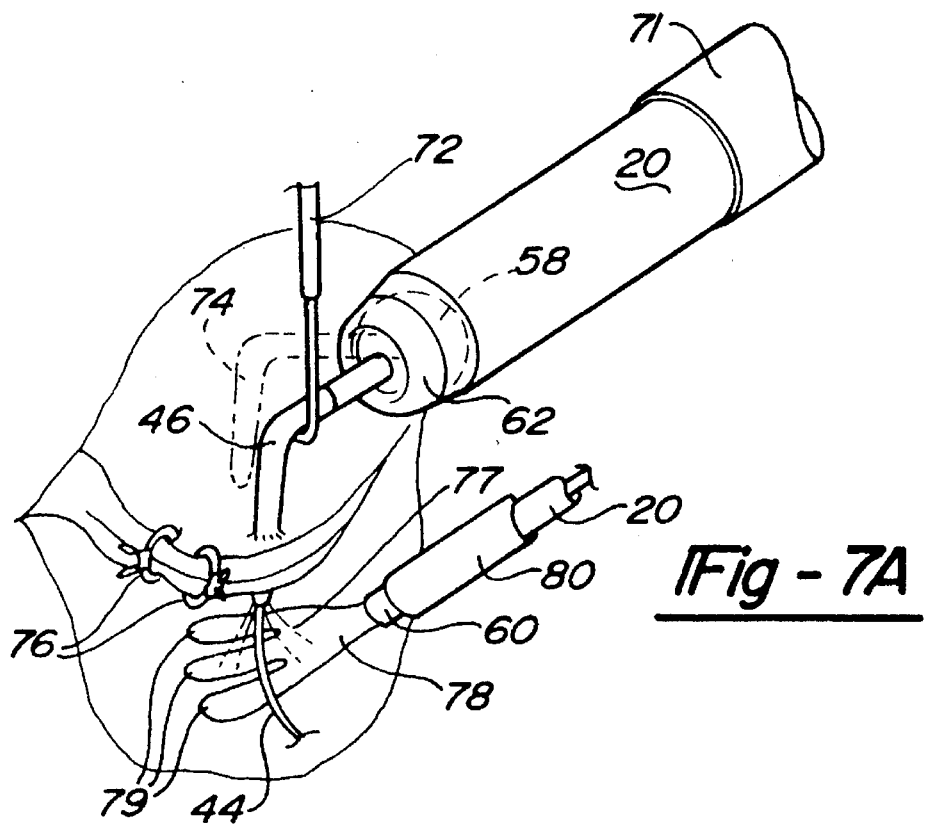
Fig - 7A
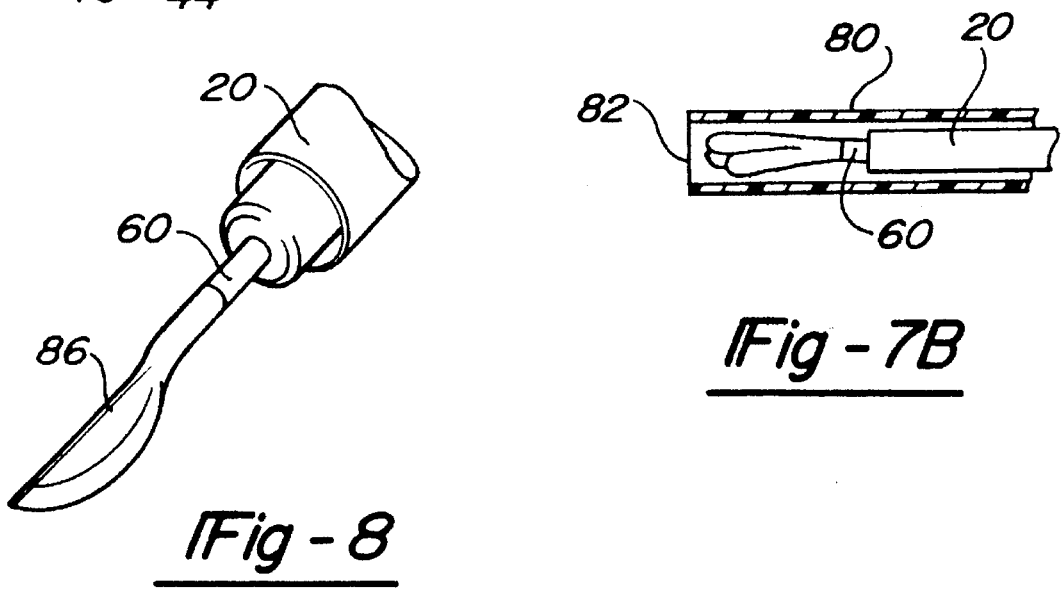
Fig - 8
Fig - 7B

LAPAROSCOPIC SURGICAL INSTRUMENT

BACKGROUND OF THE INVENTION

This application relates to a surgical instrument that is relatively easy to use for performing laparoscopic or other internal surgical procedures.

One of the newest types of surgical procedures is laparoscopic surgery. In such procedures, Several small incisions are made in a patient. A scope is inserted through one of those incisions and monitors the surgery. Surgical tools are inserted through the other incisions. By inserting a scope within the patient to monitor the surgical area, the surgeon is able to perform the surgery without actually making the otherwise necessary large incision to provide access to the area of the surgery.

In one common laparoscopic surgical procedure, $CO_2$ gas is inserted into the patient's abdomen to inflate the abdomen and create a space for the scope to be able to view the area to be treated in the surgery. Since the gas is required to inflate the abdomen, it is also necessary that each of the incisions for the surgical tools be sealed against air leakage. Thus, sheathes are typically inserted through each incision, and the surgical tools are slid within the sheath and into the patient. The surgeon monitors the surgery on a video screen by watching a video provided by the internal scope. Surgical tools extend into the patient and perform the surgery remotely, with the surgeon being guided by the video.

The use of such surgery has a great potential for many surgical procedures. The small incisions are much less stressful on the patient than the otherwise required large incisions. Until this time, however, laparoscopic surgery has been limited to certain relatively simple procedures. The reason for this perceived limitation is that many otherwise simple surgical steps become very difficult and time consuming when done with laparoscopic surgical instruments.

As one major example, suturing tissue with standard laparoscopic surgical tools is very complex. The surgeon must insert a surgical tool holding the suture needle and suture through a sheath into the patient, then grip the suturing needle with a gripping tool inserted through the same or a second sheath, and then perform the procedure of inserting the suture needle through the tissue to be sutured, and tying off the suture. The process of suturing tissue alone is enough to fatigue a surgeon. For this reason, only relatively simple surgical procedures have been adapted to laparoscopic techniques. It would, of course, be desirable to reduce the complexity of the standard surgical steps such as suturing to allow more complex surgical procedures to be performed with laparoscopic surgery techniques.

In addition, since the surgical tool must extend through the sheath, the surgical tools are typically in a relatively predefined angular orientation within the patient. It would be desirable to provide a surgical instrument which is universally adjustable relative to the barrel of the surgical instrument about any angle, and three dimensionally. In the past, laparoscopic surgical tools have only provided limited adjustment in a single two dimensional plane.

SUMMARY OF THE INVENTION

In a disclosed embodiment of this invention, a laparoscopic surgical tool allows simplification of many standard surgical step such as suturing. In one disclosed embodiment, a suture needle is formed as a hollow item at the end of a laparoscopic surgical instrument. Suture thread extends through the hollow needle, and a liquid, which is preferably a saline irrigation liquid, is driven within the barrel of the surgical instrument to carry the suture material through the hollow needle. Thus, to insert a suture into tissue with the inventive tool, the surgeon need only hook the suture needle through the tissue. The surgeon then drives the irrigation liquid outwardly through the needle, and that liquid carries the suture thread through the tissue. The suture needle can then be withdrawn, leaving the suture thread within the tissue. It is then relatively easy to tie off the suture thread to complete the suture. In a preferred embodiment of this aspect of the invention, the body of the surgical tool includes a compartment for carrying a spool of suture thread.

In another aspect of this invention, the end of the surgical instrument includes a ball connection to a surgical tool, such as a suture needle, at the end of the instrument. The ball connection allows adjustment of the tool within the patient about any angle in three dimensions. That is, the ball provides universal adjustment of the tool relative to the barrel of the surgical instrument, and also the axis of the sheath extending through the incision in the patient. In one preferred embodiment of this invention, the tool is locked at a desired angle by loosening a threaded locking system at a location outwardly of the patient. A second tool within the patient is then used to move the tool on the surgical instrument to the desired angular location. The threaded locking system is then tightened to lock the ball and hence the tool at this desired location. The surgical procedure can then be performed with the tool at this desired angle.

It may not always be possible to insert the tool through the sheath in the patient with the tool at this desired angle. It may be that the tool would extend radially outwardly beyond the barrel of the surgical instrument at the desired angle, and thus it would not move through the sheath. It is for that reason that the ability to adjust the angle after the instrument has been inserted into the patient is a very beneficial attribute of this invention.

In addition, an inflatable retractor is also disclosed within this invention. The inflatable retractor preferably has three fingers that can be inflated and used to provide retraction on tissue during the laparoscopic surgical techniques. The three finger construction provides valuable benefits in allowing retraction of the tissue.

In methods according to this invention, a suture is provided in a laparoscopic surgical procedure by inserting the inventive surgical instrument through a sheath with a hollow suture needle at the end of the instrument. A suture thread extends through the hollow suture needle. The suture needle is passed through the tissue to be sutured. Alter the suture needle has passed through the tissue, the surgeon actuates a liquid irrigation button on the handle of the inventive surgical tool. This irrigation button drives irrigation liquid, which is preferably saline irrigation fluid, outwardly through the hollow needle. This, in turn, carries the surgical thread along with the irrigation liquid. The surgical thread is thus driven further outwardly of the suture needle. The suture needle can then be withdrawn from the tissue through which it has passed, leaving the thread within the tissue. The thread can then be easily cut, and the suture knot completed.

In another method according to the present invention, the surgical instrument is inserted into the patient, and a surgical tool is provided at the end of the instrument. The surgical tool is preferably initially at an angular orientation wherein it extends generally parallel to the axis of the surgical tool. A threaded locking system on the surgical tool is then loosened. A second instrument within the patient is then used to adjust the angular orientation of the surgical tool relative to the axis of the surgical instrument. Once the tool is at the desired orientation, the threaded locking system is moved back to a locked position, wherein it locks the tool at the desired location. This allows the surgeon to position a surgical tool to any desired angle relative to the axis of the surgical instrument in the patient. These and other features of the present invention can be best understood from the following specification and drawings, of which the following is a brief description.

BRIEF DESCRIPTION OF THE DRAWINGS

FIG. 1 is a perspective view of an inventive surgical tool.

FIG. 2 is a cross-sectional view through the tool as shown in FIG. 1.

FIG. 3 is a cross-sectional view along line 3—3 as shown in FIG. 2.

FIG. 4 is a cross-sectional view along line 4—4 as shown in FIG. 2.

FIG. 5 is a cross-sectional view along line 5—5 as shown in FIG. 2.

FIG. 6 is a cross-sectional view along line 6—6 as shown in FIG. 2.

FIG. 7A is a perspective view showing a simple surgical procedure utilizing the inventive surgical tool.

FIG. 7B is a schematic view of one feature of the invention.

FIG. 8 shows the inventive surgical tool carrying a distinct type of surgical tool.

DETAILED DESCRIPTION OF A PREFERRED EMBODIMENT

An inventive surgical instrument 20 that is particularly well suited for laparoscopic surgery is shown in FIG. 1. Instrument 20 includes a body 22 having a forward cylindrical portion 24 and a handle 26. A locking cap 25 is placed at the rear of the surgical instrument for a purpose that will be described below. It should be understood that a laparoscopic surgical instrument has a very small outer diameter when compared to its length. This is because the tool must extend through the small sheath in the incision in the patient, while still reaching the location of the surgery, which is well within the patient. Thus, the reader should understand that the relative dimensions of the members in the drawing are not necessarily to scale.

Handle 26 receives two fluid connections 28 and 30. A button 32, shown schematically, provides communication with the fluid source 28, which preferably leads to a source of saline irrigation fluid. Button 34 may allow the communication of a source of suction 30 to the interior of the surgical instrument.

A spool of suture material 36 is provided within body 22. Spool 36 can be accessed by opening a door 38, and removing the spool from a shaft 40. As shown here, a new spool 42 is being placed on the shaft 40. It should be understood that the door 38 must be fluid tight, as the irrigation fluid will reach the door 38. As shown, a suture thread 44 extends from spool 36 and through a hollow suture needle 46, at the forward end of the surgical instrument 20.

As shown in FIG. 2, a locking system includes threaded end cap 25 having a threaded connection shown at 50 to a moving plug 48. A guide sleeve 52 is formed within cylinder body 24. A forward guide face 53 has a plurality of holes through which locking rods 54 extend. There are preferably three locking rods 54 which are connected by a sleeve ring 56 that abuts a ball member 58. As shown, ball member 58 includes a hollow bore with a sleeve 60. The suture thread 44 extends through sleeve 60, and sleeve 60 is connected to suture needle 46. As also shown, an end cap 62 includes an internal spherical surface 64 to mate with the outer surface of ball 58. A rear plate 66 also includes holes through which the rods 54 pass.

In one main feature of this invention, the end cap 25 can be turned to move the plug 48 axially. Rods 54 move axially with plug 48. The guide structure provided by the plates 53 and 66 insure that the rods 54 move axially, and do not rotate. When the rods 54 move axially, so does sleeve ring 56. When a surgeon wishes to adjust the angle of the tool, here needle 46, relative to the axis of the barrel 24, end cap 25 is turned in a first direction to bring the rods 54 and sleeve ring 56 to the right as shown in FIG. 2. The sleeve ring 56 is thus removed from the ball 58, and the ball may be adjusted to any desired angle in three dimensions relative to the end cap 62. Thus, by adjusting the ball 58, the angular orientation of the suture needle 46 can move to positions such as shown in phantom in 49 or 51, from the position shown at 46 in FIG. 2. As should be understood, the movement is not limited to the positions 49 and 51. Instead, the needle can be moved to any desired angular orientation in a three dimensional space about end cap 62.

As will be explained below, the surgical instrument is preferably inserted through the sheath in the patient with the suture needle 46, or other surgical instrument, extending generally parallel to the axis of the cylinder 24. This insures that the tool will not have a radially outermost extent that is beyond the radially outermost extent of the walls of cylinder 24. Cylinder 24 is preferably tightly received within the sheath to maintain an airtight connection. Once the tool is inserted into the patient, however, the end cap 25 can be loosened, and the angular orientation of the tool relative to the central axis of the cylinder 24 can be adjusted. Once the tool is at the desired angular orientation, the end cap 25 can be turned in the opposed direction and the plug 48 and rods 54 will move to the left as shown in FIG. 2. The ring 56 will again abut the ball 58, and the ball 58 will be locked at its newly adjusted position.

As also shown in FIG. 2, the connection for the saline irrigation fluid 28 extends into the body of the cylinder 24. When the surgeon actuates button 32, saline irrigation fluid is driven out of connection 28, outwardly through the sleeve 60 and out of the end of suture needle 46. This liquid will carry the suture thread 44 outwardly of the suture needle 46. As will be explained below, this will simplify the laparoscopic surgical procedure for inserting a suture into tissue.

As shown in FIG. 3, there are three rods 54, and they each extend through a hole in plate 53. The holes in the plate 53 prevent rotation of the rods 54, limiting their movement to axial reciprocation. As shown in FIG. 4, plate 53 is received with anti-rotation keys within the body of the cylinder 24. As shown in FIG. 5, the second plate 56 also includes holes to receive the rod 54, and prevent their rotation.

As shown in FIG. 6, keys 68 extend radially inwardly from the inner bore of the cylindrical housing 24 into a slot 70 formed in the guide sleeve 52. The keys extend radially inwardly from the end cap 25. The keys 68 allow the end cap 25 to freely rotate, and guide the plug 48 for axial reciprocation.

A relatively simple surgical technique is shown utilizing the inventive surgical instrument 20 in FIG. 7A. As shown in FIG. 7A, the surgical instrument 20 is inserted into a patient through a sheath 71. The suture needle 46 is at a first angular orientation relative to the axis of the surgical instrument 20. A second surgical instrument 72, shown here as simply a hook, may be inserted into the patient. The locking system, including rods 54 and sleeve ring 56 may be moved to its unlocked position, spaced from the ball 58. At that time, the second surgical tool 72 can be utilized to move the suture needle 46 to the position shown in phantom at 74. The locking system is then returned to the locked position. This is important, since in prior instruments, the relative angle of the surgical tool to the body of the surgical instrument has typically not been adjustable. There are many occasions where a surgeon would find it desirable to orientate a tool at any angular orientation in three dimensions relative to the axis of the instrument 20. However, prior laparoscopic surgical instruments have not provided this adjustability in three dimensions.

Since the surgical instrument 20 must extend through a sheath in the incision, the axis of the surgical instrument is somewhat limited. Being able to change the angular orientation of the surgical tool, here suture needle 46, relative to the axis of the surgical instrument 20, thus provides valuable benefits.

While a particular locking structure has been disclosed for locking the ball 58 at a desired location relative to the axis of the tool, it should be understood that other locking structures would come within the scope of this invention. What is most important to this invention is not the specifics of the locking structure, but rather the provision of a locking structure that can be actuated outwardly of the patient to lock the tool at a desired angular orientation and at a location within the patient, and in such a way that the tool can be adjusted three dimensionally relative to the axis of the surgical instrument.

In addition, while the suture needle 46 is shown attached to the sleeve 60, it should be understood that many other surgical instruments would also benefit from the adjustability provided by the ball 58 and the locking structure.

A second aspect of this invention is shown providing sutures 76 in the tissue. As has been previously discussed, the suture needle 46 is initially passed through the tissue to receive the suture. The irrigation fluid is then actuated, and is shown schematically at 77 leaving the end of the suture needle 46. This fluid drives the suture thread 44 outwardly of the needle 46. The surgeon may then pull the suture needle 46 back out of the tissue. It is then a relatively simple procedure to cut the suture thread 44 and tie off the knot to form the complete suture 76. The surgeon is able to perform this procedure easily, and the fatigue associated with the prior art repetitive movements necessary to perform laparoscopic suturing is eliminated.

As briefly discussed above, with the prior art laparoscopic surgical instruments, suturing has been a very time consuming procedure. For that reason, many surgeons have attempted to utilized surgical staples or clips rather than suture. For many procedures, however, suturing is more preferable. For these reasons, the laparoscopic surgical techniques have not been applied to more complex operations. With the inventive surgical tool, and the ease with which sutures can be inserted, and other steps performed, laparoscopic surgical techniques may be extended to many more complicated operations.

Another aspect of the invention shown in FIG. 7A is an expandable retractor 78. Retractor 78 includes three fingers 79 that provide a broad surface that will allow good retraction of tissue. A retractor is essentially an instrument to move tissue away from a surgical location to provide the surgeon with access to the surgical location. The several fingers 79 provide a strong holding force for the tissue to be moved.

As shown in FIG. 7B, a retractable sleeve 80 receives the deflated retractor 82 during insertion. When utilizing the surgical instrument 20 with the expandable retractor 78, the surgical instrument is inserted into the patient with the sheath 80 in its forward position and the retractor in its deflated position 82. Once inside the patient, the retractable sheath 80 is retracted, and the retractor is inflated. Retractable sheaths are known, and the details of the sheath form no portion of this invention. The irrigation fluid may be utilized to inflate the retractor 78.

FIG. 8 shows a cutting tool 86 mounted on the surgical instrument 20. Again, the sleeve 60 includes an end attachment structure that allows the attachment of many different surgical tools.

In methods according to this invention, a suture may be provided within a patient in a laparoscopic surgical technique by passing a suture thread through a hollow suture needle. The suture needle is then used to pass through the tissue to receive the suture. The liquid is then driven through the suture needle, and carries the thread outwardly of the needle. The needle may then be pulled back outwardly of the tissue, leaving the suture thread within the tissue. The suture is then easily completed.

In another method according to the present invention, the relative angular orientation of a tool at an end of a surgical instrument is modified relative to the central axis of the surgical instrument at a location internal to a patient. A surgical instrument is initially inserted through an incision in the patient in a first angular orientation. A locking system is moved to an unlocked position and the angular orientation of the tool relative to the surgical instrument is adjusted to a desired angular orientation. The locking system is then moved to lock the tool at its newly adjusted location. Preferably, the locking system includes threaded locking structure that is accessible at a location outwardly of the patient. Thus, a surgeon may adjust the angular orientation of a tool within a patient by actuating a locking system outwardly of the patient. In one embodiment, a second surgical instrument within the patient is used to move the tool when the locking structure is in the unlocked position.

A preferred embodiment of this invention has been disclosed, however a worker of ordinary skill in the art would recognize that certain modifications would come within the scope of this invention. For that reason, the following claims should be studied in order to determine the true scope and content of this invention.

I claim:

1. A surgical tool for performing internal surgery on a patient comprising:

1) an instrument body extending along an axis;

2) a tool mounted at an internal first end of said body, said tool being connected to said body such that the angular orientation of said tool relative to said axis of said body may be adjustable in three dimensions;

3) said tool being connected to a spherical shaped member that is selectively locked within said body, the angular orientation of said tool being adjusted by adjusting the position of said spherical member relative to said body, an end cap on said body provides a spherical contact surface for said spherical member; and 4) means to lock said tool at a desired angular orientation relative to said axis carried on said tool, said means to lock said tool includes a plurality of rods that are selectively axially moveable within said body to contact said spherical shaped member and hold said ball, and thus said tool, at a particular angular orientation, said rods also being moveable to an unlocked position wherein said ball may move relative to said axis.

2. A surgical instrument as recited in claim 1, wherein said rods are connected to an annular ring at an end of said rods, said ring selectively contacting said spherical member.

3. A surgical instrument as recited in claim 1, wherein a threaded connection is formed on said body at an end remote from said first end, said threaded connection providing for reciprocation of said rods between said locked and unlocked positions.

4. A surgical instrument as recited in claim 1, wherein said tool is a hollow suture needle, and a suture thread selectively extends through said hollow suture needle.

5. A surgical instrument as recited in claim 4, wherein said surgical instrument includes a connection to a source of a liquid, said liquid being selectively communicated with said bore of said suture needle to carry said suture thread outwardly of said suture needle.

6. A surgical instrument as recited in claim 5, wherein an access door is provided in said body, said access door providing access to a spool post, and a spool of suture thread being received on said spool post.

7. A surgical instrument as recited in claim 1, wherein said tool is a retractor having at least three fingers, said retractor being selectively inflated within the body of a patient.

8. A surgical instrument comprising:
1) a body extending along an axis and for extending through an incision in a patient, a suture needle mounted at a first end of said body that will be internal to the patient, a second end of said body being positioned outwardly of the patient during a surgical procedure, said suture needle being hollow said suture needle being connected to said body such that the angular orientation of said suture needle relative to said axis of said body may be adjustable in three dimensions, and means to lock said suture needle at a desired angular orientation relative to said axis after alignment;

2) a suture thread source mounted within said body, and a suture thread extending through said body and into and through said hollow needle; and 3) said body being provided with a connection for connecting to a source of a liquid wherein said connection terminates within said body at a point spaced from said hollow needle, said liquid contacting said suture thread, and carrying said suture thread outwardly through said hollow needle to drive said suture thread through said hollow needle.

9. A surgical instrument as recited in claim 8, wherein said source of suture thread is a spool mounted on a spool post in said body.

10. A surgical instrument as recited in claim 9, wherein an access door is provided within said body to allow access to said spool.

11. A surgical method comprising the steps of:
1) inserting a surgical instrument within an incision in a patient, said surgical instrument being provided with a surgical tool at an internal end, said surgical tool being at a particular angular orientation relative to an axis of a body of said surgical instrument when inserted, said surgical instrument being provided with a selectively actuatable locking structure holding said tool at said particular angular orientation;

2) moving said locking structure to an unlocked orientation;

3) adjusting the angular orientation of said tool relative to said axis of said body to a desired angular orientation, such adjustment being provided in a three dimensional space; and 4) moving said locking structure to a locked position to lock said tool at said adjusted angular orientation, said locking structure being threaded and the turning of a first threaded member causes a locking structure to reciprocate a plurality of rods to lock said tool at said adjusted position.

* * * * *